(12) United States Patent
Reddy et al.

(10) Patent No.: US 8,563,215 B2
(45) Date of Patent: Oct. 22, 2013

(54) DIAZONAPHTHOQUINONESULFONIC ACID BISPHENOL DERIVATIVE USEFUL IN PHOTO LITHOGRAPHIC SUB MICRON PATTERNING AND A PROCESS FOR PREPARATION THEREOF

(75) Inventors: Vummadi Venkat Reddy, Andhra Pradesh (IN); Vaidya Jayathirtha Rao, Andhra Pradesh (IN); Mannepalli Lakshmi Kantam, Andhra Pradesh (IN); Sunkara Sakunthala Madhavendra, Andhra Pradesh (IN); Virendra Kumar Dwivedi, Rajasthan (IN)

(73) Assignee: Council of Scientific & Industrial Research, New Delhi (IN)

( * ) Notice: Subject to any disclaimer, the term of this patent is extended or adjusted under 35 U.S.C. 154(b) by 751 days.

(21) Appl. No.: 12/532,234

(22) PCT Filed: Mar. 20, 2008

(86) PCT No.: PCT/IN2008/000169
§ 371 (c)(1),
(2), (4) Date: Sep. 21, 2009

(87) PCT Pub. No.: WO2008/117308
PCT Pub. Date: Oct. 2, 2008

(65) Prior Publication Data
US 2010/0081084 A1    Apr. 1, 2010

(30) Foreign Application Priority Data

Mar. 23, 2007 (IN) .............. 649/DEL/2007

(51) Int. Cl.
*G03F 7/022* (2006.01)
*G03F 7/30* (2006.01)
*G03F 7/38* (2006.01)
*C07C 245/12* (2006.01)
*G03F 7/023* (2006.01)

(52) U.S. Cl.
CPC ............ *G03F 7/022* (2013.01); *G03F 7/0236* (2013.01); *G03F 7/38* (2013.01); *C07C 245/12* (2013.01)
USPC ........... 430/192; 430/165; 430/193; 430/326; 430/330

(58) Field of Classification Search
CPC ......... G03F 7/022; G03F 7/0236; G03F 7/38; C07C 245/12
USPC ................ 430/165, 191, 192, 193, 326, 330; 534/556, 557
See application file for complete search history.

(56) References Cited

U.S. PATENT DOCUMENTS

| 4,812,200 | A | * | 3/1989 | Birkle et al. | 216/47 |
| 5,082,932 | A | | 1/1992 | Siegel et al. | |
| 5,182,183 | A | * | 1/1993 | Tomiyasu et al. | 430/165 |
| 5,234,793 | A | * | 8/1993 | Sebald et al. | 430/323 |
| 5,290,656 | A | * | 3/1994 | Uetani et al. | 430/165 |
| 5,362,599 | A | * | 11/1994 | Knors et al. | 430/192 |
| 5,384,228 | A | * | 1/1995 | Doi et al. | 430/192 |
| 5,401,617 | A | * | 3/1995 | Kato et al. | 430/326 |
| 5,532,107 | A | * | 7/1996 | Oie et al. | 430/192 |
| 6,559,291 | B1 | * | 5/2003 | Reddy et al. | 534/557 |
| 6,905,809 | B2 | * | 6/2005 | Eilbeck | 430/190 |
| 7,355,021 | B2 | * | 4/2008 | Reddy et al. | 534/557 |
| 2004/0185368 | A1 | | 9/2004 | Dammel et al. | |

FOREIGN PATENT DOCUMENTS

EP     0 965 580     12/1999

OTHER PUBLICATIONS

Zakrzewski, A., et al. "Method of Manufacture of aryl 2-diazo-1-oxonaphthalene-5-sulfonates for photopolymeric positive emulsions." *Chemical Abstracts, American Chemical Society, US* (1989) vol. 21, No. 110, Abstract [XP-002115190].

* cited by examiner

*Primary Examiner* — John Chu
(74) *Attorney, Agent, or Firm* — Ladas & Parry LLP

(57) ABSTRACT

The present invention provides novel diazonaphthoquinonesulfonic acid bisphenol derivatives. More particularly, the present invention relates to photo restive coating comprising alkali-soluble resin, a photoactive compound and a surfactant. The photoresist film prepared has less then one micron. The photoactive compound is soluble or swellable in aqueous alkaline solutions and is diazonaphthoquinonesulfonic bisphenol esters of the general formula (A), wherein DNQ represents a 2-Diazo-1-naphthoquinone-4-sulfonyl, 2-Diazo-1-naphthoquinone-5-sulfonyl, 1-Diazo-2-naphthoquinone-4-sulfonyl groups and R1 R1 represents an alkyl, aryl and substituted aryl groups. The invention also provides a process for coating and imaging the light-sensitive composition.

14 Claims, No Drawings

DIAZONAPHTHOQUINONESULFONIC ACID BISPHENOL DERIVATIVE USEFUL IN PHOTO LITHOGRAPHIC SUB MICRON PATTERNING AND A PROCESS FOR PREPARATION THEREOF

FIELD OF THE INVENTION

The present invention relates to novel diazonaphthoquinonesulfonic acid bisphenol derivatives. More particularly, the present invention relates to photo restive coating comprising alkali-soluble resin, a photoactive compound and a surfactant. The photoresist film prepared has less then one micron.

The photoactive compound is soluble or swellable in aqueous alkaline solutions and is diazonaphthoquinonesulfonic bisphenol esters of the general formula A,

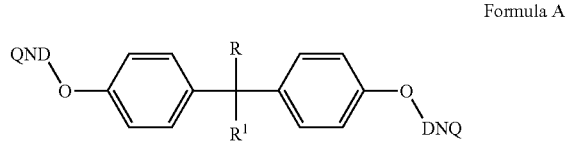

Formula A wherein DNQ represents a 2-Diazo-1-naphthoquinone-4-sulfonyl, 2-Diazo-1-naphthoquinone-5-sulfonyl, 1-Diazo-2-naphthoquinone-4-sulfonyl groups and R, $R^1$ represents an alkyl, aryl and substituted aryl groups. The invention also relates to a process for coating and imaging the light-sensitive composition.

BACKGROUND OF THE INVENTION

As positive photoresist composition there are normally used compositions comprising an alkali-soluble resin and a diazonaphthoquinone compound as a photosensitive material. Example of such composition include novolak type phenol resins, diazonaphthoquinone substituted compounds as disclosed in U.S. Pat. No. 4,173,470. Most typical examples of such composition include novolak resin composed of cresol-formaldehyde/trihydroxybenzophenonediazonaphthoquinonesulfonic ester as disclosed in L. F. Thompson, introduction to microlithography, ACS publishing Co., No. 219, pages 112 to 121.

It is known to the skilled artisan to produce positive photoresist compositions, such as those described in patent U.S. pat. No. L. A. Colom et al. U.S. Pat. No. 3,666,473 used the resin and photo activating compounds are 1:0.25, here photo activating compound is used is excess. Some of the US patents are Buhr et al. U.S. Pat. No. 5,563,018, McKean et al. U.S. Pat. Nos. 5,580,602 and 5,702,756, Clecak et al. U.S. Pat. No. 4,397,937, Sezi et al. U.S. Pat. Nos. 5,863,705 and 6,110,637, Patrascu et al. U.S. Pat. No. 5,512,700, Oberlander U.S. Pat. No. 6,077,942, Sinta et al. U.S. Pat. No. 5,917,024, Canize et al. U.S. Pat. No. 5,612,164. These include water insoluble, aqueous alkali-soluble phenol-formaldehyde novolak resin together with light sensitive materials, usually a substituted diazonaphthoquinone compounds. The resins and photosensitizers are dissolved in an organic solvent or mixture of solvents and are applied as a thin film or coating to a substrate suitable for the particular application desired.

OBJECTIVES OF THE INVENTION

The main objective of the present invention is to provide novel photo active compound of formula A.

Yet another objective of the present invention is to provide novel diazonaphthoquinonesulfonyl bisphenol esters.

Another object is to get relative thermally stable (TGA/DSC studies) sensitizers.

Yet another objective of the present invention is to provide a process for the preparation of photo active compound of formula A.

Yet another objective of the present invention is to provide a photoresist coating composition for the preparation of photoresist coating film for photilithiographic submicron patterning.

Yet another object of the present invention is to provide less than sub micron pattern of resolution.

Still another object of the present invention is to provide a process having less exposure time, less developing time, diluted developer.

SUMMARY OF THE INVENTION

Accordingly the present invention provides a photoactive compound of general formula A

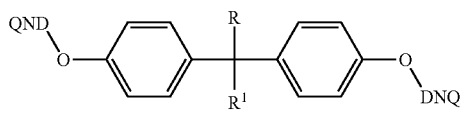

wherein DNQ represents a 2-Diazo-1-naphthoquinone-4-sulfonyl, 2-Diazo-1-naphthoquinone-5-sulfonyl, 1-Diazo-2-naphthoquinone-4-sulfonyl groups and R, $R^1$ represents an alkyl, aryl and substituted aryl groups.

In an embodiment of the present invention the compound according to claim 1, wherein the representative compounds of photoactive compound of formula A are as follows:

4-[1-(4-[(6-diazo-5-oxo-5,6-dihydro-1-naphthalenyl)sulfonyl]oxyphenyl)-1-methylpropyl]phenyl 6-diazo-5-oxo-5,6-dihydro-1-naphthalenesulfonate (18);

4-[1-(4-[(6-diazo-5-oxo-5,6-dihydro-1-naphthalenyl)sulfonyl]oxyphenyl)-1-ethylpropyl]phenyl 6-diazo-5-oxo-5,6-dihydro-1-naphthalenesulfonate (19);

4-[1-(4-[(6-diazo-5-oxo-5,6-dihydro-1-naphthalenyl)sulfonyl]oxyphenyl)-1,3-dimethylbutyl]phenyl 6-diazo-5-oxo-5,6-dihydro-1-naphthalenesulfonate (20);

4-[1-(4-[(6-diazo-5-oxo-5,6-dihydro-1-naphthalenyl)sulfonyl]oxyphenyl)cyclopentyl]phenyl 6-diazo-5-oxo-5,6-dihydro-1-naphthalenesulfonate (21);

4-[1-(4-[(3-diazo-4-oxo-3,4-dihydro-1-naphthalenyl)sulfonyl]oxyphenyl)-1-methylpropyl]phenyl 3-diazo-4-oxo-3,4-dihydro-1-naphthalenesulfonate (22);

4-[1-(4-[(3-diazo-4-oxo-3,4-dihydro-1-naphthalenyl)sulfonyl]oxyphenyl)-1-ethylpropyl]phenyl 3-diazo-4-oxo-3,4-dihydro-1-naphthalenesulfonate (23);

4-[1-(4-[(3-diazo-4-oxo-3,4-dihydro-1-naphthalenyl)sulfonyl]oxyphenyl)-1,3-dimethylbutyl]phenyl 3-diazo-4-oxo-3,4-dihydro-1-naphthalenesulfonate (24);

4-[1-(4-[(3-diazo-4-oxo-3,4-dihydro-1-naphthalenyl)sulfonyl]oxyphenyl)cyclopentyl]phenyl 3-diazo-4-oxo-3,4-dihydro-1-naphthalenesulfonate (25).

In yet another embodiment the general structure of the representative compounds of photoactive compound of formula A are as follows:

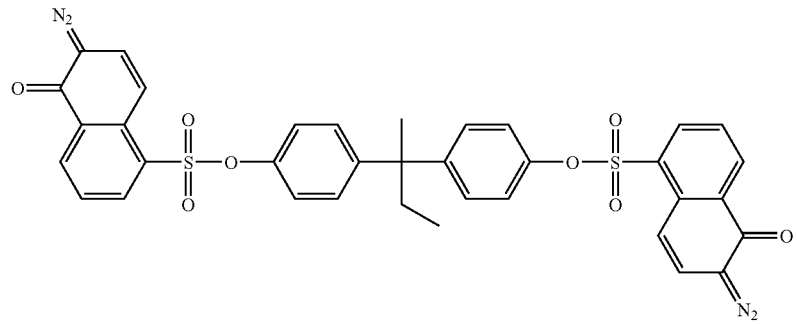
18
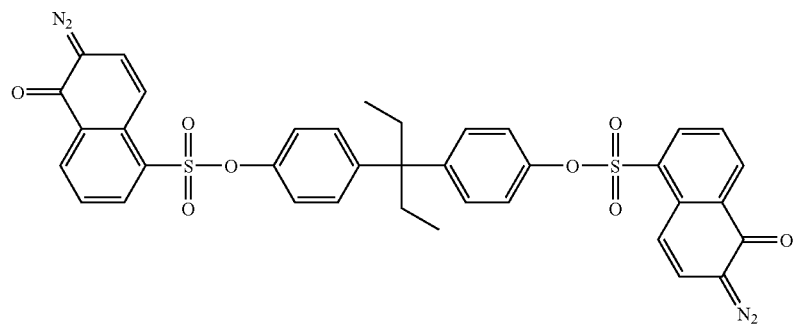
19
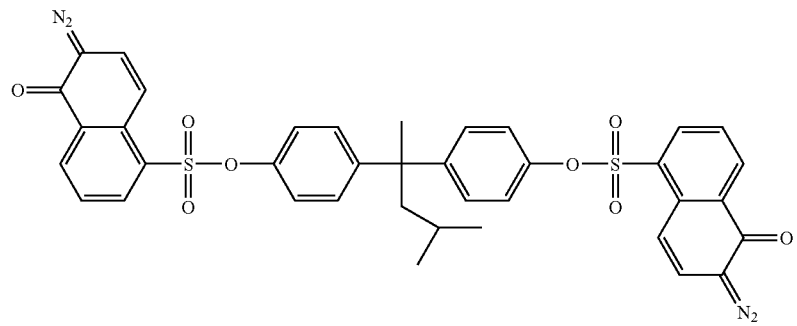
20
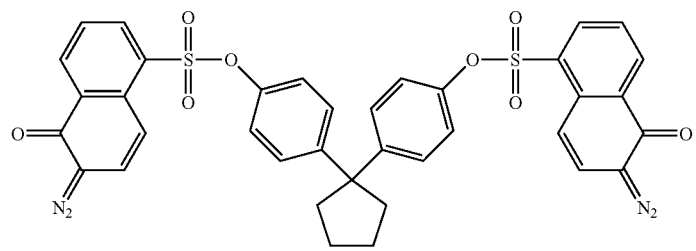
21
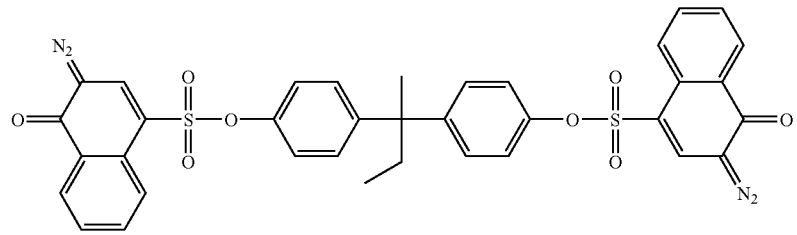
22

-continued

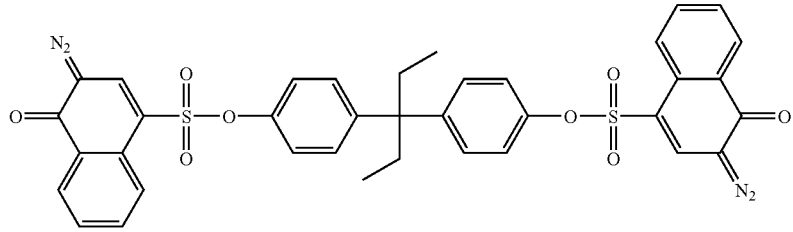

23

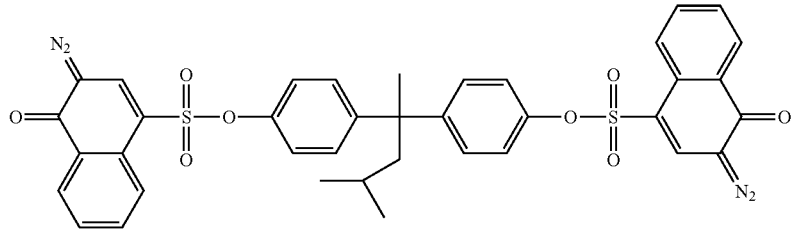

24

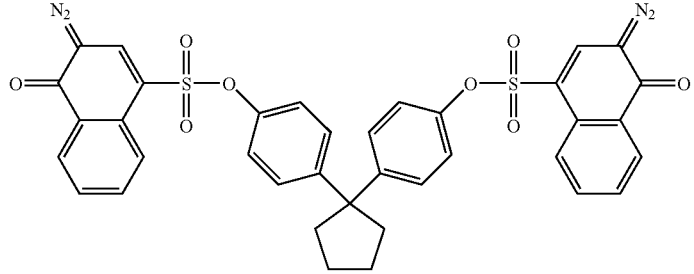

25

In yet another embodiment the photoactive compound of formula A is useful for the preparation of photoresist coating film for photilithiographic submicron pattering.

The present invention further provides a process for the preparation of Photoactive compound of general formula A

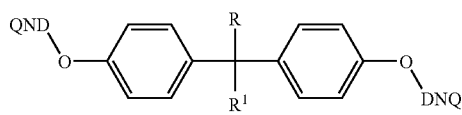

wherein DNQ represents a 2-Diazo-1-naphthoquinone-4-sulfonyl, 2-Diazo-1-naphthoquinone-5-sulfonyl, 1-Diazo-2-naphthoquinone-4-sulfonyl groups and R, $R^1$ represents an alkyl, aryl and substituted aryl groups and the said process comprising the steps of:
  a) reacting diazonapthoquinonesulfonate with triphosgene in the presence of triethylamine in dichloromethane, at a temperature of −40 to −60° C., for a period of 20-30 minutes, to obtain the corresponding diazonapthoquinonesulfonylchloride,
  b) reacting the above said diazonapthoquinonesulfonylchloride with substituted bisphenol in the presence of triethyl amine in dichloromethane, at a temperature of 0-2° C., for a period of 50-70 minutes to obtain the desired corresponding photoactive compound of formula A.

In yet another embodiment the diazonapthoquinone sulfonylchloride obtained is selected from 2-diazo-1-napththoquinone-4-sulfonyl chloride, 2-diazo-1-naphthoquinone-5-sulfonyl chloride, 1-diazo-2-naphthoquinone-4-sulfonyl chloride.

In yet another embodiment the substituted bisphenol used is selected from the group consisting of 4-[1-(4-hydroxyphenyl)-1-methylpropyl]phenol; 4-[1-ethyl-1-(4-hydroxyphenyl)propyl]phenol; 4-[1-(4-hydroxyphenyl)-1,3-dimethylbutyl]phenol; 4-[1-(4-hydroxyphenyl)cyclopentyl]phenol; 4-[1-(4-bromophenyl)-1-(4-hydroxyphenyl)pentyl]phenol; 4-[1-(4-chlorophenyl)-1-(4-hydroxyphenyl)propyl]phenol; 4-[1-(4-bromophenyl)-1-(4-hydroxyphenyl)pentyl]phenol; 4-[1-(4-fluorophenyl)-1-(4-hydroxyphenyl)propyl]phenol and 4-[1-(4-hydroxyphenyl)-1-phenylpropyl]phenol.

In yet another embodiment the representative compounds of photoactive compound of formula A obtained are as follows:
  4-[1-(4-[(6-diazo-5-oxo-5,6-dihydro-1-naphthalenyl)sulfonyl]oxyphenyl)-1-methylpropyl]phenyl 6-diazo-5-oxo-5,6-dihydro-1-naphthalenesulfonate (18);
  4-[1-(4-[(6-diazo-5-oxo-5,6-dihydro-1-naphthalenyl)sulfonyl]oxyphenyl)-1-ethylpropyl]phenyl 6-diazo-5-oxo-5,6-dihydro-1-naphthalenesulfonate (19);
  4-[1-(4-[(6-diazo-5-oxo-5,6-dihydro-1-naphthalenyl)sulfonyl]oxyphenyl)-1,3-dimethylbutyl]phenyl 6-diazo-5-oxo-5,6-dihydro-1-naphthalenesulfonate (20);
  4-[1-(4-[(6-diazo-5-oxo-5,6-dihydro-1-naphthalenyl)sulfonyl]oxyphenyl)cyclopentyl]phenyl 6-diazo-5-oxo-5,6-dihydro-1-naphthalenesulfonate (21);
  4-[1-(4-[(3-diazo-4-oxo-3,4-dihydro-1-naphthalenyl)sulfonyl]oxyphenyl)-1-methylpropyl]phenyl 3-diazo-4-oxo-3,4-dihydro-1-naphthalenesulfonate (22);
  4-[1-(4-[(3-diazo-4-oxo-3,4-dihydro-1-naphthalenyl)sulfonyl]oxyphenyl)-1-ethylpropyl]phenyl 3-diazo-4-oxo-3,4-dihydro-1-naphthalenesulfonate (23);
  4-[1-(4-[(3-diazo-4-oxo-3,4-dihydro-1-naphthalenyl)sulfonyl]oxyphenyl)-1,3-dimethylbutyl]phenyl 3-diazo-4-oxo-3,4-dihydro-1-naphthalenesulfonate (24);

4-[1-(4-[(3-diazo-4-oxo-3,4-dihydro-1-naphthalenyl)sulfonyl]oxyphenyl)cyclopentyl]phenyl 3-diazo-4-oxo-3,4-dihydro-1-naphthalenesulfonate (25).

According to the invention, there is provided a photoresist coating composition comprising a photo active compound of general formula A, an alkali soluble resin, an additive and solvent

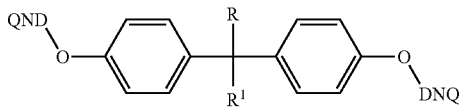

wherein DNQ represents a 2-Diazo-1-naphthoquinone-4-sulfonyl, 2-Diazo-1-naphthoquinone-5-sulfonyl, 1-Diazo-2-naphthoquinone-4-sulfonyl groups and R, $R^1$ represents an alkyl, aryl and substituted aryl groups.

In yet another embodiment the ratio of photoactive compound to phenolic resin is in the range of 1:5 to 1:12.

In yet another embodiment wherein the ratio of photoactive compound to phenolic resin used is preferably 1:10.

In yet another embodiment the photo activating compound used is selected from the group consisting of 4-[1-(4-[(6-diazo-5-oxo-5,6-dihydro-1-naphthalenyl)sulfonyl]oxyphenyl)-1-methylpropyl]phenyl 6-diazo-5-oxo-5,6-dihydro-1-naphthalenesulfonate (18);

4-[1-(4-[(6-diazo-5-oxo-5,6-dihydro-1-naphthalenyl)sulfonyl]oxyphenyl)-1-ethylpropyl]phenyl 6-diazo-5-oxo-5,6-dihydro-1-naphthalenesulfonate (19);

4-[1-(4-[(6-diazo-5-oxo-5,6-dihydro-1-naphthalenyl)sulfonyl]oxyphenyl)-1,3-dimethylbutyl]phenyl 6-diazo-5-oxo-5,6-dihydro-1-naphthalenesulfonate (20);

4-[1-(4-[(6-diazo-5-oxo-5,6-dihydro-1-naphthalenyl)sulfonyl]oxyphenyl)cyclopentyl]phenyl 6-diazo-5-oxo-5,6-dihydro-1-naphthalenesulfonate (21);

4-[1-(4-[(3-diazo-4-oxo-3,4-dihydro-1-naphthalenyl)sulfonyl]oxyphenyl)-1-methylpropyl]phenyl 3-diazo-4-oxo-3,4-dihydro-1-naphthalenesulfonate (22);

4-[1-(4-[(3-diazo-4-oxo-3,4-dihydro-1-naphthalenyl)sulfonyl]oxyphenyl)-1-ethyl propyl]phenyl 3-diazo-4-oxo-3,4-dihydro-1-naphthalenesulfonate (23);

4-[1-(4-[(3-diazo-4-oxo-3,4-dihydro-1-naphthalenyl)sulfonyl]oxyphenyl)-1,3-dimethylbutyl]phenyl 3-diazo-4-oxo-3,4-dihydro-1-naphthalenesulfonate (24);

and 4-[1-(4-[(3-diazo-4-oxo-3,4-dihydro-1-naphthalenyl)sulfonyl]oxyphenyl)cyclopentyl]phenyl 3-diazo-4-oxo-3,4-dihydro-1-naphthalenesulfonate (25).

In yet another embodiment the additive used is hexamethyldisilazane (HMDS).

In yet another embodiment the solvents used is selected from the group consisting of 2-ethoxy ethyl acetate, methoxyacetoxy propane, n-butyl acetate, ethyl lactate, ethyl 3-ethoxy propionate and propylene glycol alkyl ether acetates.

In yet another embodiment the solvent used is preferably 2-ethoxy ethyl acetate (cellosolve acetate).

In yet another embodiment the phenolic resin used is a novolak resin.

In yet another embodiment the photoresist composition is useful for the preparation of photilithiographic submicron pattering film.

The present invention further provides a process for imaging a photoresist coating and the said process comprising the steps of:

a) coating a substrate with a photoresist coating composition to form a photoresist coating film, characterized in that the said photoresist coating film comprising an alkali soluble resin and a photoactive compound, b) subjecting the above said photoresist film coated substrate to image-wise exposure to radiation, c) optionally, subjecting the above said photoresist coating to post exposure baking and d) treating the above said photoresist film coated substrate with an aqueous alkaline solution to obtain the desired image patterning substrate.

In an embodiment of the present invention the photoactive compound used is having a general formula A

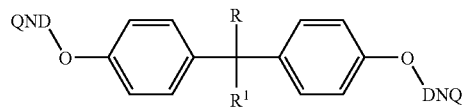

wherein DNQ represents a 2-Diazo-1-naphthoquinone-4-sulfonyl, 2-Diazo-1-naphthoquinone-5-sulfonyl, 1-Diazo-2-naphthoquinone-4-sulfonyl groups and R, $R^1$ represents an alkyl, aryl and substituted aryl groups In yet another embodiment the aqueous alkaline solution used is an aqueous solution of a base selected from the group consisting of tetramethylammonium hydroxide, sodium hydroxide, potassium hydroxide, ammonium hydroxide, ethanolamine, sodium phosphates, sodium carbonate and sodium metasilicate.

In yet another embodiment the aqueous alkaline solution used is preferably tetramethylammonium hydroxide.

In still another embodiment the width, as a line width and thickness of the photoresist film is <0.5 micron and 1-1.5 micron, respectively.

DETAIL DESCRIPTION OF THE INVENTION

A light-sensitive composition, especially suitable for preparation of photolithographic printing plates, comprising a water insoluble resinous binder which is soluble or swellable in aqueous alkaline solutions and diazonaphthoquinonesulfonic bisphenol esters of the general formula I

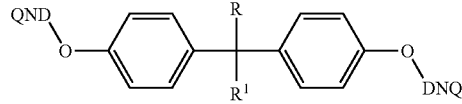

Where DNQ represents a 2-Diazo-1-naphthoquinone-4-sulfonyl, 2-Diazo-1-naphthoquinone-5-sulfonyl, 1-Diazo-2-naphthoquinone-4-sulfonyl groups and R, $R^1$ represents an alkyl, aryl and substituted aryl groups.

A positive photoresist composition includes (A) An alkali-soluble resin, in which part of phenolic hydroxyl groups, (B) A diazonaphthoquinonesulfonic esters and (C) A compound, which generates an acid upon irradiation of light with a wavelength of 365 nm. This positive photoresist composition can form a fine pattern of about sub micron (0.5 micron) in the photolithographic process using i-ray (365 nm) is excellent in focal depth range properties in such an ultra fine region and has a high sensitivity.

Photoresist compositions are used in micro lithography processes for making miniaturized electronic components such as in the fabrication computer chips and integrated circuits. Generally, in these processes a coating film of a photo resist composition is first applied to a substrate material, such as silicon wafers used for making integrated circuits. The coated substrate is then baked to evaporate any solvent in the photoresist composition and to fix the coating onto the substrate. The baked coated surface of the substrate is next subjected to an image wise exposure to radiation This radiation exposure causes a chemical transformation in the exposed areas of the coated surface. Visible light, ultraviolet (UV) light, electron beam and X-ray radiant energy are the radiation types commonly used today in micro lithographic processes. After this image wise exposure, the coated substrate is treated with a developer solution to dissolve and remove either the radiation-exposed or the unexposed areas of the coated surface of the substrate.

There are two types of photo resist composition, negative working and positive working. When negative working photoresist compositions are exposed image-wise to radiation, the areas of the resist composition exposed to the radiation become less soluble to a developer solution (e.g. a cross-linking reaction occurs) while the unexposed area of the photoresist coating remain relatively soluble in such a solution. Thus, treatment of an exposed negative-working resist with a developer causes removal of the non-exposed areas of the photoresist coating and the creation of a negative image in the coating. Thereby uncovering a desired portion of the underlying substrate surface on which the photoresist composition was deposited.

On the other hand, when positive-working photoresist compositions are exposed image-wise to radiation, those areas of the photoresist composition exposed to the radiation become more soluble to the developer solution (e.g. a rearrangement reaction occurs) while those areas not exposed remain relatively insoluble to the developer solution. Thus treatment of an exposed positive-working photoresist with the developer causes removal of the exposed areas of the coating and the creation of a positive image in the photoresist coating. Again, a desired portion of the underlying substrate surface is uncovered.

After this development operation, the now partially unprotected substrate may be treated with a substrate-etchant solutions, plasma gases, or have metal or metal composition deposited in the spaces of the substrate where the photoresist coating was removed during development. The areas of the substrate where the photoresist coating still remains are protected. Later, the remaining areas of the photoresist coating may be removed during a stripping operation, leaving a patterned substrate surface. In some instances it is desirable to heat treat the remaining photoresist layer, after the development step before the etching step, to increase its adhesion to the underlying substrate.

Positive-acting photoresists comprising novolak resins and diazonaphthoquinone compounds as photoactive compounds are well known in the art. Condensing formaldehyde and one or more multi-substituted phenols, in the presence of an acid catalyst, such as oxalic acid, typically produce Novolak resins. Photoactive compounds are generally obtained by reacting multihydroxyphenolic compounds with diazonaphthoquinonesulfonic acids or their derivatives. Novolaks may also be reacted with diazonaphthoquinonesulfonic acid and combined with a polymer.

Additives, such as surfactants, are often added to a photoresist composition to improve the coating uniformity of the photoresist film.

The prepared photoresist composition solution, can be applied to a substrate by spin coating, for example the photoresist solution can be adjusted with respect to the percentages of solids content, in order to provide coating of the desired thickness, given the type of spinning equipment utilized and the amount of time allowed for the spinning process.

The photoresist coatings produced by the desired procedure are particularly suitable for application to silicon/silicon dioxide oxide coated wafers, such as are utilized in the production of microprocessors and other miniaturized integrated circuits components. The substrate may also comprise various polymeric resins especially transparent polymers such as novolak resin. The substrate may have an adhesion promoted layer of a suitable, such as one containing HMDS.

Photoresist sample are filtered with first two prefiltered of porosity 2 micron. Then filtration by 0.45 micron filters twice. Similarly filtration by 0.20 micron filters twice.

For the preparation of photolithographic plate, we have taken 3 g of novolak resin in 10 ml of cellosolve acetate stirred for 10 mints, for this solution 300 mg of photoactivating compound is added, stirred for 10 mints. This photoresist material was filtered through 0.2 micron filters to remove undissolved particles. The viscosity of the photoresist composition is 20 cSt. After completion of filtration this photoresist material is ready for coating on silicon wafer. Before coating silicon wafer, silicon wafer cleaning is important. First conc. $H_2SO_4$ washing followed by fuming $HNO_3$ washing to remove inorganic impurities after this, the wafer was washed with D.I water several times, then with appropriate organic solvents (acetone, MeOH) to remove any water insoluble other impurities. After completion of washing dried in oven at 150° C. for 30 mints.

The prepared photoresist material was coated on the silicon wafer using with 2000-4000 RPM speed and one can get 1.5-1.0 micron thickness layer on the silicon plate. After completion of coating, photoresist coated silicon wafer are put in oven at 90° C. for 30 mints to remove volatile solvents from the coating (this is called soft baking). After completion of soft bake, photomask is aligned on the photoresist coated silicon wafer and exposed to UV light (365 nm for 10 sec.

After completion of operations developed photoresist wafers are hard bake at 120° C. for 30 mints. All this operations are conducted under yellow light/amber safe light. After completion of these operations the wafers are developed using tetramethylammoniumhydroxide (TMAH), very diluted aqueous alkaline solution to remove exposed areas of the photoresist, in the presence of UV light diazonaphthoquinonesulfonic acid bisphenol derivative loses molecular nitrogen leading to the formation of ketocarbene which rearranges to a unstable ketene and this in the presence of solvent medium, finally formation of corresponding indene carboxylic acid takes place. Thus formed acid goes into 2.38% developer aqueous alkaline solution with in 15 sec, development is very good one can get very fine pattern with fingers opened up at 0.5 micron. The results obtained are given in Table.

POSITIVE PHOTORESIST FORMULATIONS: OBSERVATION TABLE

| S. No | Novolak resin g | Photo sensitizer g | EEA mL | Spin Coating speed rpm | Thickness μm | Exposure time Sec | Dev. Time Sec | Remarks |
|---|---|---|---|---|---|---|---|---|
| 1 | 3 g | 300 mg | 10 | 2000 | 1.5 | 15-25 | 65 | Pattern open |
| 2 | 3 g | 300 mg | 10 | 2500 | 1.5 | 15-25 | 65 | Pattern open |
| 3 | 3 g | 300 mg | 10 | 3000 | 1.5 | 15-20 | 60 | Pattern open |
| 4 | 3 g | 300 mg | 10 | 3500 | 1.0 | 15-20 | 60 | Pattern open |
| 5 | 3 g | 300 mg | 10 | 4000 | 1.0 | 15-20 | 60 | Pattern open |

Under Lying Layer: oxide;
Lab Temp: 25° C.;
Lab Humidity: 52%;
Resist Amount: 2 ml;
Prebaking Temp: 90° C.;
Prebaking Time: 30 min;
Mask: XC 1705;
Develop: 100 ml of DI water in 25 ml of developer (MF CD-26 Micro Posit);
Post Bake: 120° C.;
Post Bake Time: 30 min;

These novel sensitizers have better dissolution property compare with the conventional photoresists available in the literature/market.

The following examples are given by the way of illustration and therefore should not be construed to limit the scope of the invention.

Synthesis of Novolak Resin:

51.90 g (0.480 mole) m-Cresol, 1.94 g (0.017 mole) p-Cresol, 13.86 g (0.113 mole) 2,3-Xylenol, 43.62 g (1.454 mole) aqueous solution of formaldehyde were charged in a three-necked flask of one-liter capacity equipped with a stirrer, a reflux condenser and a thermometer, and 0.226 g (0.001 mole) oxalic acid dihydrate was added thereto while stirring the mixture at 90° C. After 30 minutes, the bath temperature was raised to 130° C., and the reaction mixture was further stirred for 3 hours and 30 minutes under reflux. Subsequently, the reflux condenser was replaced with a Liebig condenser, and the bath temperature was raised to 200° C. Over about 1 hour, followed by removal of unreacted formalin, water and the like. After the distillation the reaction was carried out further 1 hour under atmospheric pressure, the pressure was gradually reduced to 1 mm Hg and unreacted monomers and the like were distilled off. The distillation under reduced pressure took 2 hours.

The temperature was lowered to room temperature and the melted alkali-soluble novolak resin was recovered (Scheme 1). The weight average molecular weight of the thus-obtained novolak resin was 2400-5400 in terms of polystyrene.

Scheme 1

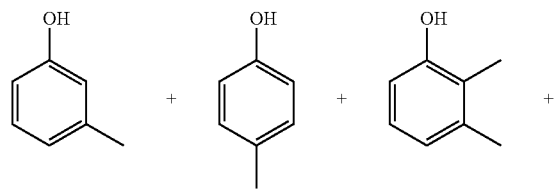

Preparation of Bisphenols:

New DNQ esters were prepared and used as new Photoactivating compounds. In this regard Bisphenols prepared as given below Phenol and ketone were mixed in the presence of dry hydrochloric acid gas (H$^+$) (Scheme 2) to get various bisphenols and are characterized by H-NMR & GC-MS.

Scheme 2

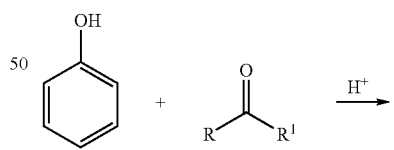

(1)R = Me, R$^1$ = Et, (2) R═R$^1$ = Et, (3)R = Me, R$^1$ = iso-Bt, (4)R = Me, R$^1$ = Ph,
(5)R = Me, R$^1$ = p-Me-Ph, (6)R = Me, R$^1$ = p-F-Ph, (7)R = Me, R$^1$ = p-Cl-Ph,
(8)R = Me, R$^1$ = p-Br-Ph, (9)R = Et, R$^1$ = Ph, (10)R = Et, R$^1$ = p-OH-Ph,
(11)R = Et, R$^1$ = p-F-Ph, (12)R = Et, R$^1$ = p-Cl-Ph, (13)R = Et, R$^1$ = p-Br-Ph,
(14)R = Bt, R$^1$ = Ph, (15)R = Bt, R$^1$ = p-Br-Ph, (16) R═R$^1$ = Cyclopenyl,
(17)R═R$^1$ = Cycloheptyl 1) 4-[1-(4-hydroxyphenyl)-1-methylpropyl]phenol

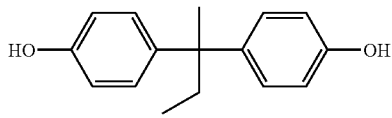 [SMILES: CCC(C)(c1ccc(O)cc1)c1ccc(O)cc1]

$^1$H-NMR (CDCl$_3$): δ 0.70 (t, 3H), 1.50 (m, 3H), δ 2.05 (q, 2H), 6.65 (m, 4H), 6.95 (m, 4H); IR: 3289, 2964, 1509, 1235, 830 cm$^{-1}$. Mass: (GC-MS): m/z 242 (M$^+$), 207, 182, 166, 125, 58.

2) 4-[1-ethyl-1-(4-hydroxyphenyl)propyl]phenol

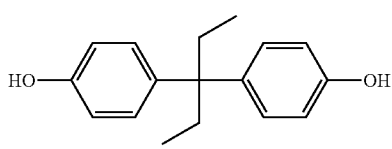 [SMILES: CCC(CC)(c1ccc(O)cc1)c1ccc(O)cc1]

$^1$H-NMR (CDCl$_3$): δ 1.10 (t, 6H) 2.45 (q, 4H), 6.86 (m, 4H), 7.20 (m, 4H); IR: 3289, 2969, 1509, 1235, 830, 558 cm$^{-1}$. Mass: (GC-MS): m/z 256 (M$^+$) 247, 211, 102, 44.

3) 4-[1-(4-hydroxyphenyl)-1,3-dimethylbutyl]phenol

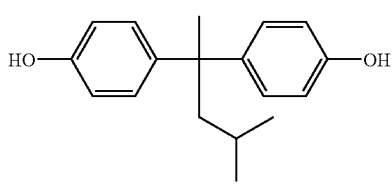 [SMILES: CC(C)CC(C)(c1ccc(O)cc1)c1ccc(O)cc1]

$^1$H-NMR (CDCl$_3$): δ 0.90 (d, 6H), 2.10 (s, 3H), 2.30 (m, 2H), 6.86 (m, 4H), 7.15 (m, 4H); IR: 3347, 2965, 1882, 1509, 1238, 1177, 827, 552 cm$^{-1}$. Mass: (GC-MS): m/z 270 (M$^+$), 253, 207, 191, 135, 96, 73.

4) 4-[1-(4-hydroxyphenyl)-1-phenylethyl]phenol

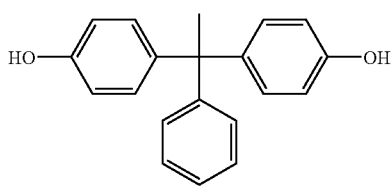 [SMILES: CC(c1ccccc1)(c1ccc(O)cc1)c1ccc(O)cc1]

$^1$H-NMR (CDCl$_3$): δ 2.58 (s, 3H), 6.86 (m, 4H), 7.15 (m, 4H), 7.40 (m, 2H), 7.50 (m, 1H), 7.95 (m, 2H); IR: 3347, 3028, 2965, 1882, 1612, 1509, 1238, 827 cm$^{-1}$. Mass: (GC-MS): m/z 290(M$^+$), 281, 267, 253, 218, 207, 191, 177, 73.

5) 4-[1-(4-hydroxyphenyl)-1-(4-methylphenyl)ethyl]phenol

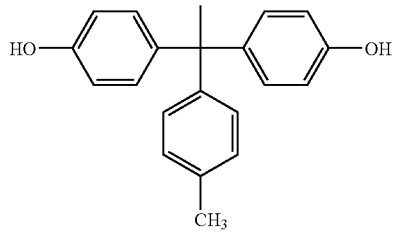 [SMILES: Cc1ccc(C(C)(c2ccc(O)cc2)c2ccc(O)cc2)cc1]

$^1$H-NMR (CDCl$_3$): 2.37 (s, 3H), 2.55 (s, 3H), 6.85 (m, 4H), 7.20 (m, 4H), 7.85 (m, 4H); IR: 3342, 2964, 1510, 1237, 1176, 826, 522 cm$^{-1}$. Mass: (GC-MS): m/z 304 (M$^+$), 262, 147, 72 (Me-Ph-Me)

6) 4-[1-(4-fluorophenyl)-1-(4-hydroxyphenyl)ethyl]phenol

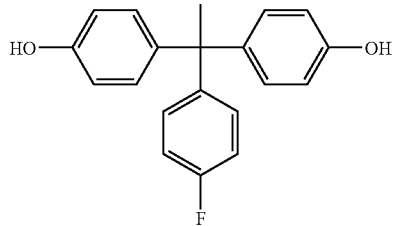 [SMILES: CC(c1ccc(O)cc1)(c1ccc(O)cc1)c1ccc(F)cc1]

$^1$H-NMR (CDCl$_3$): δ 2.62 (s, 3H), 6.85 (m, 4H), 7.20 (m, 4H), 8.0 (m, 4H); IR: 3342, 2964, 1510, 1237, 1176, 826, 522 cm$^{-1}$. Mass: (GC-MS): m/z 308 (M$^+$), 281, 269, 253, 207, 191, 85, 71, 57.

7) 4-[1-(4-chlorophenyl)-1-hydroxyphenyl)ethyl]phenol

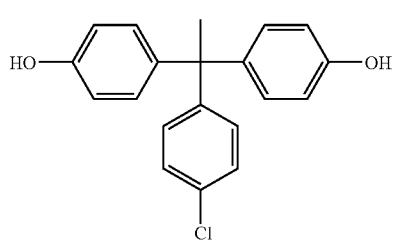 [SMILES: CC(c1ccc(O)cc1)(c1ccc(O)cc1)c1ccc(Cl)cc1]

$^1$H-NMR (CDCl$_3$): δ 2.58 (s, 3H), 6.85 (m, 4H), 7.18 (m, 4H), 7.40(m, 2H), 7.85 (m, 2H); IR: 3342, 2964, 1510, 1237, 1176, 826, 522 cm$^{-1}$. Mass: (GC-MS): m/z 324 (M$^+$), 281, 207, 133, 67.

8) 4-[1-(4-bromophenyl)-1-(4-hydroxyphenyl)ethyl]phenol

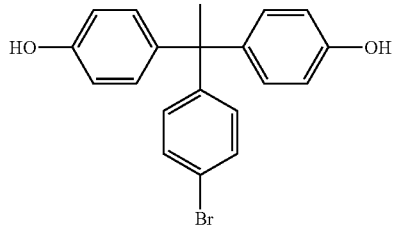 [SMILES: CC(c1ccc(O)cc1)(c1ccc(O)cc1)c1ccc(Br)cc1]

$^1$H-NMR (CDCl$_3$): δ 2.55 (s, 3H), 6.80 (m, 4H), 7.18 (m, 4H), 7.55 (m, 2H), 7.78 (m, 2H); IR: 3342, 2964, 1510, 1237, 1176, 826, 522 cm$^{-1}$. Mass: (GC-MS): m/z 369 (M$^+$) 355, 281, 221, 207, 147, 73.

9) 4-[1-(4-hydroxyphenyl)-1-phenylpropyl]phenol

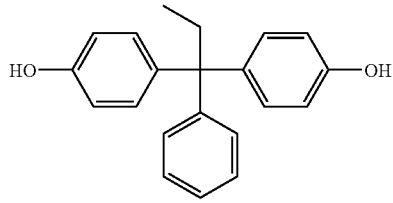 [SMILES: CCC(c1ccccc1)(c1ccc(O)cc1)c1ccc(O)cc1]

$^1$H-NMR (CDCl$_3$): δ 1.25 (t, 3H), 3.0 (q, 2H), 6.86 (m, 4H), 7.15 (m, 4H), 7.40 (m, 2H), 7.50 (m, 1H), 7.95(m, 2H); IR: 3347, 2965, 1882, 1509, 1238, 827, 552 cm$^{-1}$. Mass: (GC-MS): m/z 304 (M$^+$), 262, 207, 191, 147, 119, 91, 72.

10) 4-[1,1-di(4-hydroxyphenyl)propyl]phenol

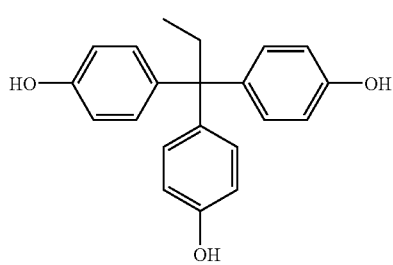 [SMILES: CCC(c1ccc(O)cc1)(c1ccc(O)cc1)c1ccc(O)cc1]

$^1$H-NMR (CDCl$_3$): δ 1.20 (t, 3H), 2.95 (q, 2H), 6.85 (m, 6H), 7.25 (m, 6H); IR: 3347, 2965, 1598, 1509, 1238, 827, 552 cm$^{-1}$. Mass: (GC-MS): m/z 320 (M), 121, 118, 66.

11) 4-[1-(4-fluorophenyl)-1-(4-hydroxyphenyl)propyl]phenol

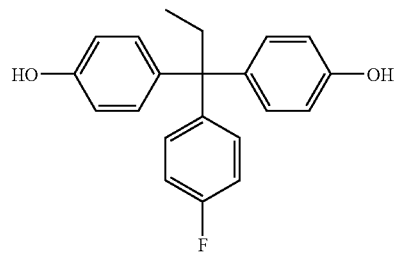 [SMILES: CCC(c1ccc(O)cc1)(c1ccc(O)cc1)c1ccc(F)cc1]

$^1$H-NMR (CDCl$_3$): δ 1.25 (t, 3H), 2.95 (q, 2H), 6.80 (m, 4H), 7.15 (m, 4H), 7.95 (m, 4H); IR: 3342, 2964, 1510, 1237, 1176, 826, 522 cm$^{-1}$. Mass: (GC-MS): m/z 322 (M$^+$), 309, 269, 253.

12) 4-[1-(4-chlorophenyl)-1-(4-hydroxyphenyl)propyl]phenol

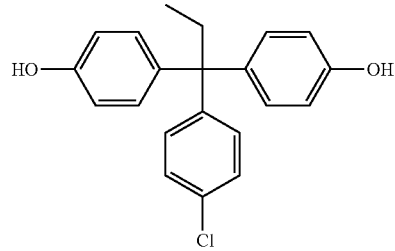 [SMILES: CCC(c1ccc(O)cc1)(c1ccc(O)cc1)c1ccc(Cl)cc1]

$^1$H-NMR (CDCl$_3$): δ 1.20 (t, 3H), 2.90 (q, 2H), 6.85 (m, 4H), 7.18 (m, 4H), 7.40 (m, 2H), 7.90 (m, 2H); IR: 3342, 2964, 1510, 1237, 1176, 826, 522 cm$^{-1}$. Mass: (GC-MS): m/z 383(M$^+$), 341, 327, 281, 147, 63, 73.

13) 4-[1-(4-bromophenyl)-1-(4-hydroxyphenyl)propyl]phenol

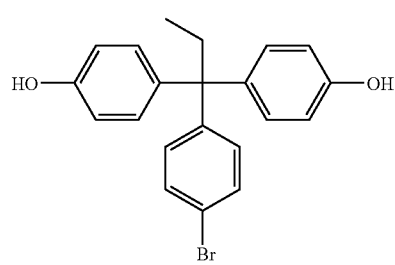 [SMILES: CCC(c1ccc(O)cc1)(c1ccc(O)cc1)c1ccc(Br)cc1]

$^1$H-NMR (CDCl$_3$): δ 1.25 (t, 3H), 2.95 (q, 2H), 6.85 (m, 4H), 7.20 (m, 4H), 7.45 (m, 2H), 7.84 (m, 2H); IR: 3342, 2964, 1510, 1237, 1176, 826, 522 cm$^{-1}$. Mass: (GC-MS): m/z 383(M$^+$), 341, 327, 281, 147, 83, 73.

14) 4-[1-(4-hydroxyphenyl)-1-phenylpentyl]phenol

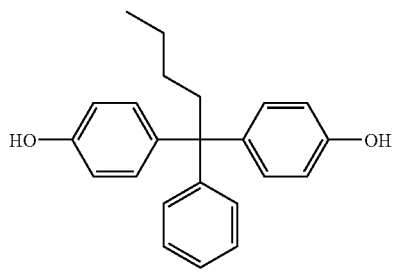 [SMILES: CCCCC(c1ccccc1)(c1ccc(O)cc1)c1ccc(O)cc1]

$^1$H-NMR (CDCl$_3$): δ 0.95 (t, 3H), 1.37 (m, 2H), 1.70 (m, 2H), 2.94 (t, 2H), 6.86 (m, 4H), 7.14 (m, 4H), 7.40 (m, 2H), 7.50 (m, 1H), 7.94(m, 2H); IR: 3302, 2969, 1597, 1509, 1235, 830, 558 cm$^{-1}$. Mass: (GC-MS): m/z 332 (M$^+$), 281, 253, 239, 207, 182, 167, 152, 105, 73.

15) 4-[1-(4-bromophenyl)-1-(4-hydroxyphenyl)pentyl]phenol

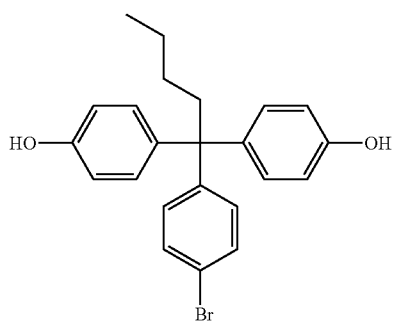 [SMILES: CCCCC(c1ccc(O)cc1)(c1ccc(O)cc1)c1ccc(Br)cc1]

$^1$H-NMR (CDCl$_3$): δ 0.95 (t, 3H), 1.40 (m, 2H), 1.70 (m, 2H), 2.90 (t, 2H), 6.86 (m, 4H), 720 (m, 4H), 7.55 (m, 2H), 7.80 (m, 2H); IR: 3342, 2964, 1510, 1237, 1176, 826, 522 cm$^{-1}$. Mass: (GC-MS): m/z 411(M$^+$), 373, 355, 341, 299, 281, 225, 207, 193, 129, 73, 55.

16) 4-[1-(4-hydroxyphenyl)cyclopentyl]phenol

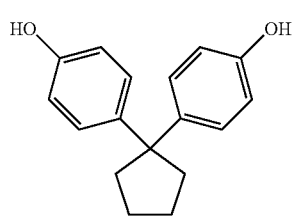 [SMILES: Oc1ccc(C2(c3ccc(O)cc3)CCCC2)cc1]

$^1$H-NMR (CDCl$_3$): δ 1.50 (m, 4H), 2.20 (m, 4H), 6.70 (m, 4H), 7.05 (m, 4H); IR: 3342, 2964, 1510, 1237, 1176, 826, 522 cm$^{-1}$. Mass: (GC-MS): m/z 254 (M$^+$), 207, 191, 177, 133, 96.

17) 4-[1-(4-hydroxyphenyl)cycloheptyl]phenol

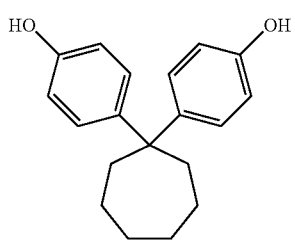 [SMILES: Oc1ccc(C2(c3ccc(O)cc3)CCCCCC2)cc1]

$^1$H-NMR (CDCl$_3$): δ 1.70 (m, 4H), 2.50 (m, 8H), 6.80 (m, 4H), 7.17 (m, 4H); IR: 3342, 2964, 1510, 1237, 1176, 826, 522 cm$^{-1}$. Mass: (GC-MS): m/z 282 (M$^+$), 269, 253, 239, 225, 207, 133.

Synthesis of New Photoactivating Compounds:

We have synthesized the photoactivating compounds (Scheme 3), such as, a 2-Diazo-1-naphthoquinone-4-sulfonyl, 2-Diazo-1-naphthoquinone-5-sulfonyl, 1-Diazo-2-naphthoquinone-4-sulfonyl groups. These photoactivating compounds are attached to the above mentioned bisphenols, and R, R$^1$ represents an alkyl, aryl and substituted aryl groups, such that one can get variety of new photoactivating compounds. The data for selected new compounds (18-25) are given below.

Scheme 3

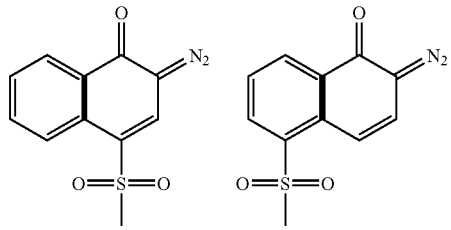

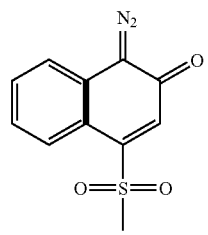

18) 4-[1-(4-(6-diazo-5-oxo-5,6-dihydro-1-naphthale-nyl)sulfonyl]oxyphenyl)-1-methylpropyl]phenyl 6-diazo-5-oxo-5,6-dihydro-1-naphthalenesulfonate

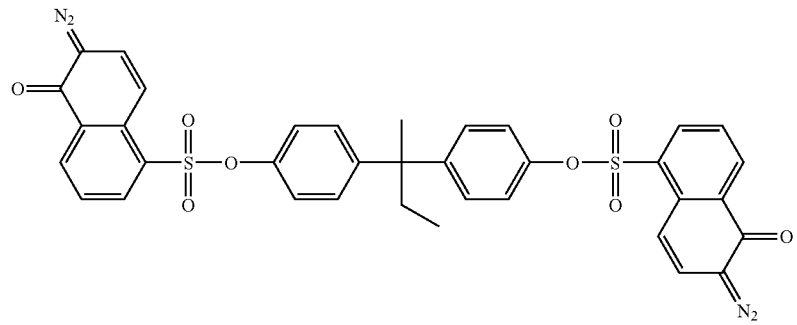

$^1$H-NMR (CDCl$_3$): δ 0.70 (t, 3H), 1.45 (s, 3H), 1.95 (q, 2H), 6.65 (m, 4H), 6.95 (m, 4H), 7.30 (d, 1H), 7.40 (m, 1H), 7.60 (d, 1H), 8.65 (m, 2H); IR: 3445, 2164, 2119, 1860, 1597, 1406, 1174, 783, 598 cm$^{-1}$. Mass: (ESI): m/z 729 (M$^{+Na}$) 695, 410, 369, 352, 172, 102; UV: λ$_{max}$=346 nm (ε=12370 cm$^{-1}$, M$^{-1}$).

19) 4-[1-(4-[(6-diazo-4-oxo-5,6-dihydro-1-naphtha-lenyl)sulfonyl]oxyphenyl)-1-ethylpropyl]phenyl 6-diazo-5-oxo-5,6-dihydro-1-naphthalenesulfonate

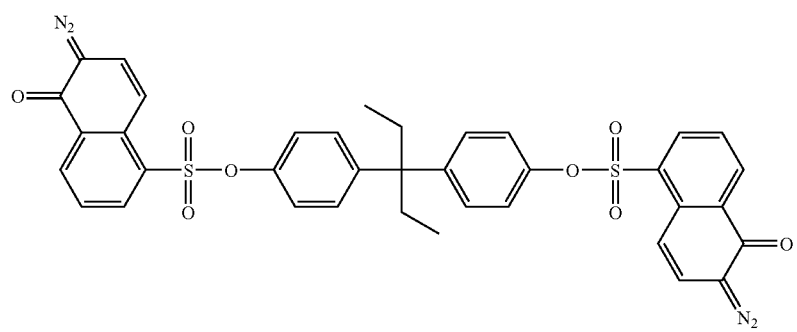

$^1$H-NMR (CDCl$_3$): δ 0.75 (t, 3H) 2.54 (q, 2H), 6.86 (m, 4H), 7.14 (m, 4H), 7.33 (d, 1H), 7.40 (d, 1H), 7.70 (m, 1H), 8.44 (d, 2H); IR: 3423, 3067, 2161, 2113, 1620, 1598, 1405, 1263, 1175, 782 cm$^{-1}$. Mass: (ESI): m/z 743 (M$^{+Na}$), 675, 511, 381, 349, 102 UV: λ$_{max}$=348 nm (ε=22579 cm$^{-1}$, M$^{-1}$).

20) 4-[1-(4-[(6-diazo-5-oxo-5,6-dihydro-1-naphthalenyl)sulfonyl]oxyphenyl)-1,3-dimethylbutyl]phenyl 6-diazo-5-oxo-5,6-dihydro-1-naphthalenesulfonate

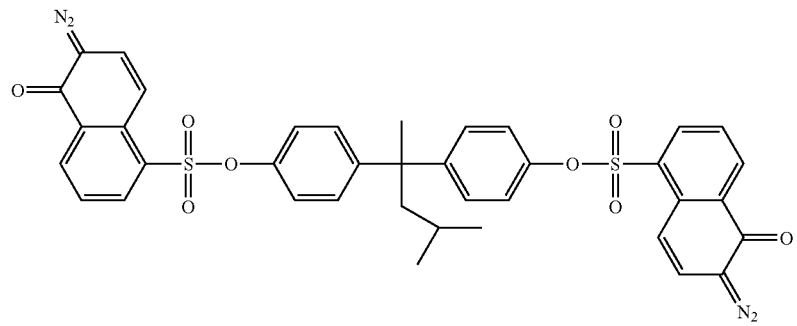

$^1$H-NMR (CDCl$_3$): δ 0.70 (d, 6H), 1.457 (s, 3H), 1.73 (m, 1H), 2.0 (d, 2H), 6.70 (m, 4H), 6.90 (m, 4H), 7.45 (d, 1H), 7.60 (d, 1H), 7.90 (d, 1H), 8.40 (m, 2H); IR: 3427, 2163, 2119, 1861, 1597, 1174, 783, 593 cm$^{-1}$. Mass: (ESI): m/z 757 (M$^{+Na}$), 102, 60 UV: λ$_{max}$=351 nm (ε=21778 cm$^{-1}$, M$^{-1}$).

21) 4-[1-(4-[(6-diazo-5-oxo-5,6-dihydro-1-naphthalenyl)sulfonyl]oxyphenyl)cyclopentyl]phenyl 6-diazo-5-oxo-5,6-dihydro-1-naphthalenesulfonate

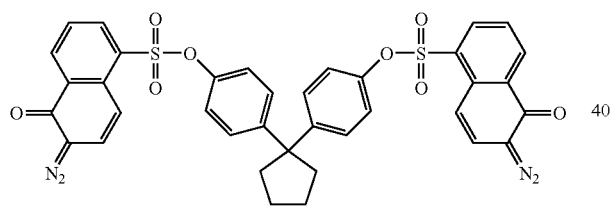

$^1$H-NMR (CDCl$_3$): δ 1.20 (m, 4H), 3.0 (m, 4H), 6.67 (m, 4H), 7.10 (m, 4H), 7.40 (m, 1H), 7.50 (m, 1H), 8.10 (m, 1H), 8.55 (d, 2H); IR: 3071, 2116, 1729, 1597, 1369, 1196, 867, 786, 559 cm$^{-1}$. Mass: (ESI): m/z 741 (M$^{+Na}$) 102, 85, 60; UV: λ$_{max}$=353 nm (ε=23690 cm$^{-1}$, M$^{-1}$).

22) 4-[1-(4-[(3-diazo-4-oxo-3,4-dihydro-1-naphthalenyl)sulfonyl]oxyphenyl)-1-methylpropyl]phenyl 3-diazo-4-oxo-3,4-dihydro-1-naphthalenesulfonate

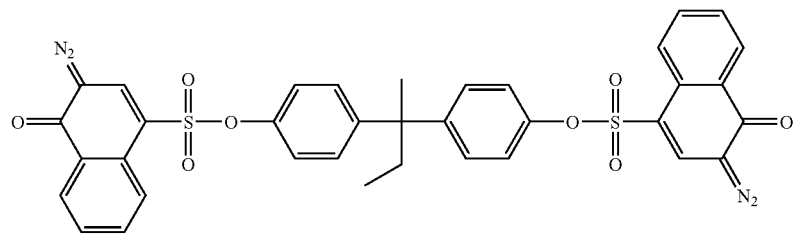

$^1$H-NMR (CDCl$_3$): δ 0.70 (t, 3H), 1.42 (s, 3H), 1.98 (q, 2H), 6.70 (m, 4H), 6.95 (m, 4H), 7.45 (m, 1H), 7.70 (m, 1H), 7.85 (s, 1H); 8.15 (m, 1H); 8.50 (d, 1H); IR: 3511, 3103, 2344, 2160, 2117, 1619, 1599, 1267, 1038, 780, 627 cm$^{-1}$. Mass: (ESI): m/z 729 (M$^{+Na}$), 214, 119, 91; UV: λ$_{max}$=346 nm (ε=11051 cm$^{-1}$, M$^{-1}$).

23) 4-[1-(4-(3-diazo-4-oxo-3,4-dihydro-1-naphthale-nyl)sulfonyl]oxyphenyl)-1-ethylpropyl]phenyl 3-diazo-4-oxo-3,4-dihydro-1-naphthalenesulfonate

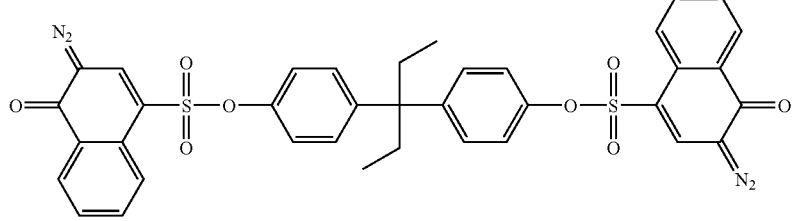

$^1$H-NMR (CDCl$_3$): δ 1.0 (t, 3H) 2.45 (q, 2H), 6.75 (m, 4H), 7.14 (m, 4H), 7.45 (m, 1H), 7.65 (m, 1H), 7.90 (s, 1H), 8.20 (m, 1H), 8.60 (d, 1H); IR: 3384, 3089, 2224, 2161, 1777, 1611, 1601, 1191, 769, 640 cm$^{-1}$. Mass: (ESI): m/z 743 (M$^{+Na}$) 737, 675, 102, 74;

UV: λ$_{max}$=346 nm (ε=14381 cm$^{-1}$, M$^{-1}$).

24) 4-[1-(4-[(3-diazo-4-oxo-3,4-dihydro-1-naphtha-lenyl)sulfonyl]oxyphenyl)-1,3-dimethylbutyl]phenyl 3-diazo-4oxo-3,4-dihydro-1-naphthalenesulfonate

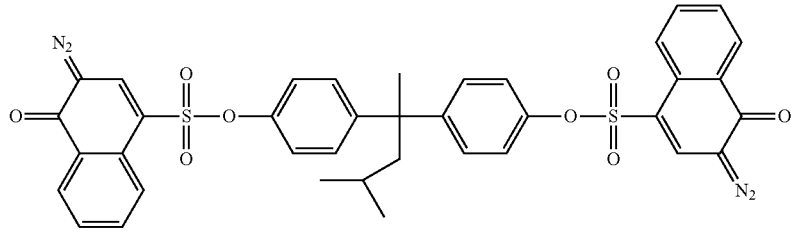

$^1$H-NMR (CDCl$_3$): δ 0.89 (d, 6H), 1.457 (s, 3H), 1.73 (m, 1H), 1.83 (d, 2H), 6.86 (m, 4H), 7.14 (m, 4H) 7.50 (m, 1H), 7.65 (m, 1H), 7.95 (s, 1H), 8.20 (m, 1H), 8.65 (d, 1H); IR: 3091, 2113, 1858, 1693, 1595, 1379, 1181, 972, 791 cm$^{-1}$. Mass: (ESI): m/z 757 (M$^{+Na}$) 327, 102, 60; UV: λ$_{max}$=347 nm (ε=15276 cm$^{-1}$, M$^{-1}$).

25) 4-[1-(4-[(3-diazo-4-oxo-3,4-dihydro-1-naphtha-lenyl)sulfonyl]oxyphenyl)cyclopentyl]phenyl 3-diazo-4-oxo-3,4-dihydro-1-naphthalenesulfonate

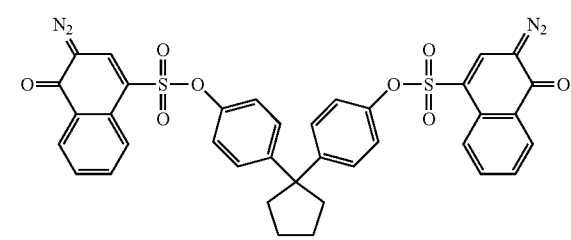

$^1$H-NMR (CDCl$_3$): δ 1.20 (m, 4H), 3.0 (m, 4H), 6.67 (m, 4H), 7.35 (m , 1H), 7.60 (m, 1H), 7.90 (s, 1H), 8.30 (m, 1H), 8.70 (d, 1H); IR: 3438, 3078, 2937, 2168, 2107, 1597, 1364, 1446, 870, 561 cm$^{-1}$. Mass: ESI): m/z 741 (M$^{+Na}$), 225, 199, 161, 107; UV: λ$_{max}$=349 nm (ε=12070 cm$^{-1}$, M$^{-1}$).

EXAMPLE 1

General Typical Procedure for the Preparation of Diazonaphthoquinone Sulfonicacid Bisphenol Derivatives (Excluding Light)

Sodium salt of diazonaphthoquinonesulfonate (2.72 g, 0.01 mol) was taken in to 25 mL of dichloromethane and cooled to −50° C. Added triethylamine (2.02 g, 0.02 mol) to the above solution and maintained the temperature at −50° C. Then added triphosgene (3.2 g, 0.01 mol) in 15 mL dichloromethane very slowly and maintaining the temperature at −50° C. with stirring over a period of 20 min. The reaction mixture was stirred magnetically for 60 min at −50° C. and then the reaction mixture was brought to 0° C. The conversion of diazonaphthalenesulfonic acid or its sodium salt to the corresponding sulfonylchloride can be conveniently monitored by UV-Visible absorption spectrometry. To the reaction mixture added bisphenol (0.0047 mol) in 3 ml dichloromethane and followed by triethylamine (2.02 g, 0.02 mol) in 3 mL dichloromethane. Stirring was continued for the 60 min at 0° C. Reaction mixture was brought to room temperature, dichloromethane and triethylamine was distilled off at room temperature under vacuum. The remaining solid residue was mixed with cold soda water (0.9 g, Na$_2$CO$_3$ in 25 mL water) and stirred for 10 min. The solid was filtered, washed with copious amounts of water and dried in a vacuum desiccator containing phosphorus pentoxide. All these operations were conducted in a yellow room/dark room. After the isolation of the ester product was photolysed (365 nm) to ascertain photoactivating property. The ester formation can be conveniently monitored by UV-Visible absorption spectrometry. The yield is quantitative.

EXAMPLE 2

General Typical Procedure for the Preparation of Diazonaphthoquinone Sulfonicacid Bisphenol Derivatives (Excluding Light)

Sodium salt of diazonaphthoquinonesulfonate (5.44 g, 0.02 mol) was taken in to 50 mL of dichloromethane end cooled to −50° C. Added triethylamine (4.04 g, 0.04 mol) to the above solution and maintained the temperature at −50° C. Then added triphosgene (6.26 g, 0.021 mol) in 30 mL dichloromethane very slowly and maintaining the temperature at −50° C. with stirring over a period of 20 min. The reaction mixture was stirred magnetically for 60 min at −50° C. and then the reaction mixture as brought to 0° C. The conversion of diazonaphthalenesulfonic acid or its sodium salt to the corresponding sulfonylchloride can be conveniently monitored by UV-Visible absorption spectrometry. To the reaction mixture added bisphenol (0.0095 mol) in 6 mL dichloromethane and followed by triethylamine (4.04 g, 0.04 mol) in 6 mL dichloromethane. Stirring was continued for the 60 min at 0° C. Reaction mixture was brought to room temperature, dichloromethane and triethylamine was distilled off at room temperature under vacuum. The remaining solid residue was mixed with cold soda water (1.8 g, $Na_2CO_3$ in 50 mL water) and stirred for 10 min. The solid was filtered, washed with copious amounts of water and dried in a vacuum desiccator containing phosphorus pentoxide. All these operations were conducted in a yellow room/dark room. After the isolation of the ester product was photolysed (365 nm) to ascertain photoactivating property. The ester formation can be conveniently monitored by UV-Visible absorption spectrometry. The yield is quantitative.

EXAMPLE 3

General Typical Procedure for the Preparation of Diazonaphthoquinone Sulfonicacid Bisphenol Derivatives (Excluding Light)

Sodium salt of diazonaphthoquinonesulfonate (8.16 g, 0.03 mol) was taken in to 75 mL of dichloromethane and cooled to −50° C. Added triethylamine (6.06 g, 0.06 mol) to the above solution and maintained the temperature at −50° C. Then added triphosgene (9.20 g, 0.031 mol) in 45 mL dichloromethane very slowly and maintaining the temperature at −50° C. with stirring over a period of 20 min. The reaction mixture was stirred magnetically for 60 min at −50° C. and then the reaction mixture was brought to 0° C. The conversion of diazonaphthalenesulfonic acid or its sodium salt to the corresponding sulfonylchloride can be conveniently monitored by UV-Visible absorption spectrometry. To the reaction mixture added bisphenol (0.0142 mol) in 9 mL dichloromethane and followed by triethylamine (9.20 g, 0.031 mol) in 9 mL dichloromethane. Stirring was continued for the 60 min at 0° C. Reaction mixture was brought to room temperature, dichloromethane and triethylamine was distilled off at room temperature under vacuum. The remaining solid residue was mixed with cold soda water (2.7 g, $Na_2CO_3$ in 75 mL water) and stirred for 10 min. The solid was filtered, washed with copious amounts of water and dried in a vacuum desiccator containing phosphorus pentoxide. All these operations were conducted in a yellow room/dark room. After the isolation of the ester product was photolysed (365 nm) to ascertain photoactivating property. The ester formation can be conveniently monitored by UV-Visible absorption spectrometry. The yield is quantitative.

EXAMPLE 4

General Typical Procedure for the Preparation of Diazonaphthoquinone Sulfonicacid Bisphenol Derivatives (Excluding Light)

Sodium salt of diazonaphthoquinonesulfonate (10.88 g, 0.04 mol) was taken in to 100 mL of dichloromethane and cooled to −50° C. Added triethylamine (8.08 g, 0.08 mol) to the above solution and maintained the temperature at −50° C. Then added triphosgene (12.17 g, 0.041 mol) in 60 mL dichloromethane very slowly and maintaining the temperature at −50° C. with stirring over a period of 20 min. The reaction mixture was stirred magnetically for 60 min at −50° C. and then the reaction mixture was brought to 0° C. The conversion of diazonaphthalenesulfonic acid or its sodium salt to the corresponding sulfonylchloride can be conveniently monitored by UV-Visible absorption spectrometry. To the reaction mixture added bisphenol (0.0188 mol) in 15 mL dichloromethane and followed by triethylamine (8.08 g, 0.08 mol) in 15 mL dichloromethane. Stirring was continued for the 60 min at 0° C. Reaction mixture was brought to room temperature, dichloromethane and triethylamine was distilled off at room temperature under vacuum. The remaining solid residue was mixed with cold soda water (3.6 g, $Na_2CO_3$ in 100 mL water) and stirred for 10 min. The solid was filtered, washed with copious amounts of water and dried in a vacuum desiccator containing phosphorus pentoxide. All these operations were conducted in a yellow room/dark room. After the isolation of the ester product was photolysed (365 nm) to ascertain photoactivating property. The ester formation can be conveniently monitored by UV-Visible absorption spectrometry. The yield is quantitative.

General Procedure for the Preparation of Bisphenols:

Gaseous hydrogen chloride was passed gradually into a mixture of two moles phenol and one mole of ketone while stirring and maintaining the mixture at temperature between 15-20° C. A total of hydrogen chloride was added in a period of 3 hours. Reaction mixture color change is observed. The mixture was then dissolved with heating in chlorobenzene and washed with two portions of nearly boiling water to remove hydrogen chloride there from the chlorobenzene layer was next neutralized. Water, chlorobenzene and unreacted phenol were distilled off at atmospheric pressure. The pressure was then reduced and the distillation continued until phenol no longer distilled from the mixture. The yield of the reaction is quantitative.

Advantages

The various advantages of this innovative process are given below:
1. The advantage of this process is that one can use new & variety of diazonaphthoquinonesulfonic acid bisphenol derivatives for the preparation of photolithographic plates.
2. We have prepared several bisphenols to prepare new diazonaphthoquinonesulfonic acid bisphenyl derivatives.
3. The composition of the present invention is particularly useful and advantageous when used with mid ultraviolet light (300-335 nm) exposure. They are however, also useful with near ultraviolet tight, and visible light (365-450 nm), with X-rays, and with electron team irradiation.
4. Exposing the photoresist composition to radiation of wavelength 300-500 nm, preferably 365 nm.
5. The advantage is we have achieved a fine pattern line width of <0.5 micron.
6. The advantage is exposure time is very lets i.e. 10 sec.
7. The advantage is we have used very diluted alkaline aqueous solution.

8. The procedure develop for making sensitizers is ONE POT preparation.
9. The sulfonylchloride and esterification reactions can be conveniently monitored by UV Visible absorption spectrometer.
We claim:
1. A photoactive compound having a formula as follows:
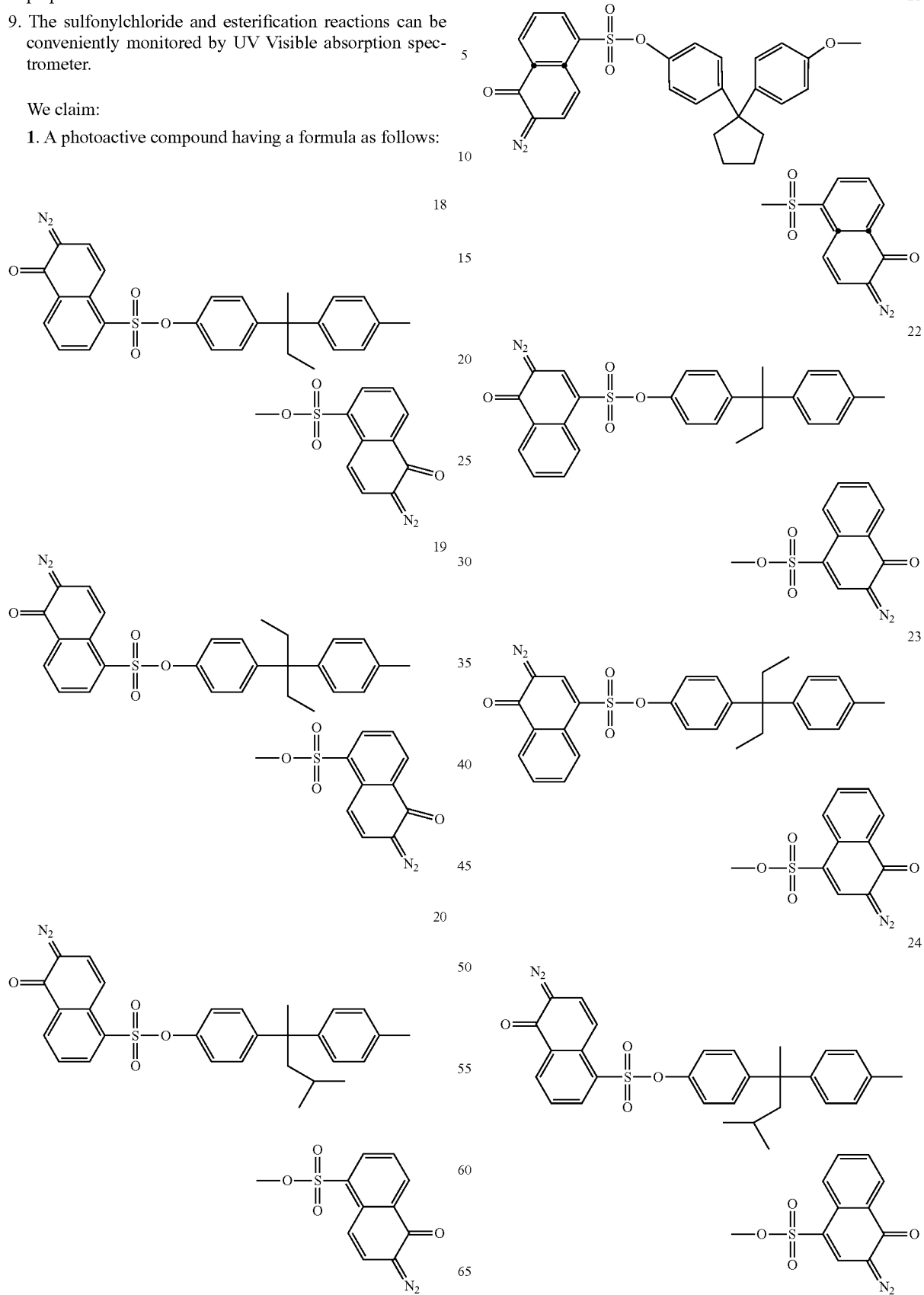

-continued

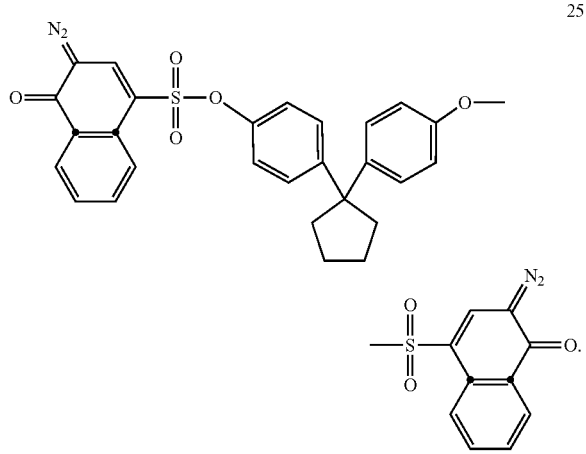

2. A process for the preparation of a photoactive compound selected from the group consisting of
4-[1-(4-[(6-diazo-5-oxo-5,6-dihydro-1-naphthalenyl)sulfonyl]oxyphenyl)-1-methylpropyl[phenyl 6-diazo-5-oxo-5,6-dihydro-1-naphthalenesulfonate (18);
4-[1-(4-[(6-diaz)-5-oxo-5,6-dihydro-1naphthalenyl)sulfonyl]oxyphenyl)-1-ethylpropyl]phenyl 6-diazo-5-oxo-5,6-dihydro-1-naphthalenesulfonate (19);
4-[1-(4-[(6-diazo-5-oxo-5,6-dihydro-1-naphthalenyl)sulfonyl]oxyphenyl)-1,3-dimethylbutyl]phenyl 6-diazo-5-oxo-5,6-dihydro-1-naphthalenesulfonate (20);
4-[1-(4-[(6-diazo-5-oxo-5,6-dihydro-1-naphthalenyl)sulfonyl]oxyphenyl) cyclopentyl]phenyl 6-d[iota]azo-5-oxo-5,6-dihydro-1-naphthalenesulfonate (21);
4-[1-(4-[(3-diazo-4-oxo-3,4-dihydro-1-naphthalenyl)sulfonyl]oxyphenyl)-1-methylpropyl]phenyl 3-diazo-4-oxo-3,4-dihydro-1-naphthalenesulfonate (22);
4-[1-(4-[(3-diazo-4-oxo-3,4-dihydro-1-naphthalenyl)sulfonyl]oxyphenyl)-1-ethylpropyljphenyl 3-diazo-4-oxo-3,4-dihydro-1-naphthalenesulfonate (23);
4-[1-(4-[(3-diazo-4-oxo-3,4-dihydro-1-naphthalenyl)sulfonyl]oxyphenyl)-1,3-dimethylbutyl]phenyl 3-diazo-4-oxo-3,4-dihydro-1-naphthalenesulfonate (24);
4-[1-(4-[(3-diazo-4-oxo-3,4-dihydro-1-naphthalenyl)sulfonyl]oxyphenyl) cyclopentyl]phenyl 3-diazo-4-oxo-3,4-dihydro-1-naphthalenesulfonate (25), said process comprising the steps of:
a) reacting a diazonapthoquinonesulfonate selected from 2-diazo-1-naphthoquinone-4-sulfonate and 2-diazo-1-naphthoquinone-5-sulfonate with triphosgene in the presence of triethylamine in dichloromethane, at a temperature of −40 to −60° C., for a period of 20-30 minutes, to obtain the corresponding diazonapthoquinonesulfonylchloride,
b) reacting the above said diazonapthoquinonesulfonylchloride with a substituted bisphenol selected from the group consisting of 4-[1-(4-hydroxyphenyl)-1-methylpropyl]phenol; 4-[1-ethyl-1-(4-hydroxyphenyl)propyl]phenol; 4-[1-(4hydroxyphenyl)-1,3-dimethylbutyl]phenol; 4-(4-hydroxyphenyl)cyclopentyl]phenol and mixtures thereof;
in the presence of triethyl amine in dichloromethane, at a temperature of 0-2° C., for a period of 50-70 minutes to obtain the corresponding photoactive compound.
3. A photoresist coating composition comprising a photo active compound, selected from the group consisting of:
4-[1-(4-[(6-diazo-5-oxo-5,6-dihydro-1-naphthalenyl)sulfonyl]oxyphenyl)-1-methylpropyl]phenyl 6-diazo-5-oxo-5,6-dihydro-1-naphthalenesulfonate (18);
-4-[1-(4-[(6-diazo-5-oxo-5,6-dihydro-1-naphthalenyl)sulfonyl]oxyphenyl)-1-ethylpropyl]phenyl 6-diazo-5-oxo-5,6-dihydro-1-naphthalenesulfonate (19);
4-[1-(4-[(6-diazo-5-oxo-5,6-dihydro-1-naphthalenyl)sulfonyl]oxyphenyl)-1,3-dimethylbutyl]phenyl 6-diazo-5-oxo-5,6-dihydro-1-naphthalenesulfonate (20);
4-[1-(4-[(6-diazo-5-oxo-5,6-dihydro-1-naphthalenyl)sulfonyl]oxyphenyl) cyclopentyl]phenyl 6-diazo-5-oxo-5,6-dihydro-1-naphthalenesulfonate (21);
4-[1-(4-[(3-diazo-4-oxo-3,4-dihydro-1-naphthalenyl)sulfonyl]oxyphenyl)-1-methylpropyl]phenyl 3-diazo-4-oxo-3,4-dihydro-1-naphthalenesulfonate (22);
4-[1-(4-[(3-diazo-4-oxo-3,4-dihydro-1-naphthalenyl)sulfonyl]oxyphenyl)-1-ethyl propyl]phenyl 3-diazo-4-oxo-3,4-dihydro-1-naphthalenesulfonate (23);
4-[1-(4-[(3-diazo-4-oxo-3,4-dihydro-1-naphthalenyl)sulfonyl]oxyphenyl)-1,3-dimethylbutyl]phenyl 3-diazo-4-oxo-3,4-dihydro-1-naphthalenesulfonate(24); and
4-[1-(4-[(3-diazo-4-oxo-3,4-dihydro-1-naphthalenyl)sulfonyl]oxyphenyl) cyclopentyl]phenyl 3-diazo-4-oxo-3,4-dihydro-1-naphthalenesulfonate (25)and mixtures thereof, an alkali soluble resin, an additive and solvent.
4. The photoresist composition according to claim 3, wherein the ratio of photoactive compound to phenolic resin is in the range of 1:5 to 1:12.
5. The photoresist composition according to claim 3, wherein the ratio of photoactive compound to phenolic resin used is preferably 1:10.
6. The photoresist composition according to claim 3, wherein the additive used is hexamethyldisilazane (HMDS).
7. The photoresist composition according to claim 3, wherein the solvents used is selected from the group consisting of 2-ethoxy ethyl acetate, methoxyacetoxy-propane, n-ibutyl acetate, ethyl lactate, ethyl 3-ethoxy propionate and propylene glycol alkyl ether acetates.
8. The photoresist composition according to claim 3, wherein the solvent used is 2-ethoxy ethyl acetate (cellosolve acetate).
9. The photoresist composition according to claim 3, wherein the phenolic resin used is a novolak resin.
10. A process for imaging a photoresist coating and the said process comprising the steps of:
a) coating a substrate with a photoresist coating composition to form a photoresist coating film, characterized in that the said photoresist coating film comprising an alkali soluble resin and a photoactive compound
selected from the group consisting of
4-[1-(4-[(6-diazo-5-oxo-5,6-dihydro-1-naphthalenyl)sulfonyl]oxyphenyl)-1-methylpropyl]phenyl 6-diazo-5-oxo-5,6-dihydro-1-naphthalenesulfonate (18);
4-[1-(4-[(6-diazo-5-oxo-5,6-dihydro-1-naphthalenyl)sulfonyl]oxyphenyl)-1-ethylpropyl]phenyl 6-diazo-5-oxo-5,6-dihydro-1-naphthalenesulfonate (19);
4-[1-(4-[(6-diazo-5-oxo-5,6-dihydro-1-naphthalenyl)sulfonyl]oxyphenyl)-1,3-dimethylbutyljphenyl 6-diazo-5-oxo-5,6-dihydro-1-naphthalenesulfonate (20);
4-[1-(4-[(6-diazo-5-oxo-5,6-dihydro-1-naphthalenyl)sulfonyl]oxyphenyl) cyclopentyl]phenyl 6-diazo-5-oxo-5,6-dihydro-1-naphthalenesulfonate (21);
4-[1-(4-[(3-diazo-4-oxo-3,4-dihydro-1-naphthalenyl)sulfonyl]oxyphenyl)-1-methylpropyljphenyl 3-diazo-4-oxo-3,4-dihydro-1-naphthalenesulfonate (22);

4-[1-(4-[(3-diazo-4-oxo-3,4-dihydro-1-naphthalenyl)sul-
fonyl]oxyphenyl)-1-ethylpropyl]phenyl 3-diazo-4-oxo-
3,4-dihydro-1-naphthalenesulfonate (23);

4-[1-(4-[(3-diazo-4-oxo-3,4-dihydro-1-naphthalenyl)sul-
fonyl]oxyphenyl)-1,3-dimethylbutyl]phenyl 3-diazo-4-
oxo-3,4-dihydro-1-naphthalenesulfonate (24);

4-[1-(4-(3-,diazoˆoxo-3,4-dihydro-1-naphthalenyl)sulfo-
nyl]oxyphenyl) cyclopentyl]phenyl 3-diazo-4-oxo-3,4-
dihydro-1-naphthalenesulfonatc (25), b) subjecting the above said photoresist film coated substrate to image-wise exposure to radiation, c) optionally, subjecting the above said photoresist coating to post exposure baking and d) treating the above said photoresist film coated substrate with an aqueous alkaline solution to obtain the desired image patterning substrate.

11. The process according to claim 10, wherein the aqueous alkaline solution used is an aqueous solution of a base selected from the group consisting of tetramethylammonium hydroxide, sodium hydroxide, potassium hydroxide, ammonium hydroxide, ethanolamine, sodium phosphates, sodium carbonate and sodium metasilicate.

12. The process according to claim 10, wherein the aqueous alkaline solution used is tetramethylammonium hydroxide.

13. The process according to claim 10, wherein the desired image has a width, as a line width and thickness of the photoresist film is <0.5 micron and 1-1.5 micron, respectively.

14. Photoactive compound selected from the group consisting of

4-[1-(4-[(6-diazo-5-oxo-5,6-dihydro-1-naphthalenyl)sul-
fonyl]oxyphenyl)-1-methylpropyl]phenyl 6-diazo-5-
oxo-5,6-dihydro-1-naphthalenesulfonate (18);

4-[1-(4-[(6-diazo-5-oxo-5,6-dihydro-1-naphthalenyl)sul-
fonyl]oxyphenyl)-1-ethylpropyl]phenyl 6-diazo-5-
oxo-5,6-dihydro-1-naphthalenesulfonate (19);

4-[1-(4-[(6-diazo-5-oxo-5,6-dihydro-1-naphthalenyl)sul-
fonyl]oxyphenyl)-1,3-dimethylbutyljphenyl 6-diazo-5-
oxo-5,6-dihydro-1-naphthalenesulfonate (20);

4-[1-(4-[(6-diazo-5-oxo-5,6-dihydro-1-naphthalenyl)sul-
fonyl]oxyphenyl) cyclopentyl]phenyl 6-diazo-5-oxo-5,
6-dihydro-1-naphthalenesulfonate (21);

4-[1-(4-[(3-diazo-4-oxo-3,4-dihydro-1-naphthalenyl)sul-
fonyl]oxyphenyl)-1-methylpropyljphenyl 3-diazo-4-
oxo-3,4-dihydro-1-naphthalenesulfonate (22);

4-[1-(4-[(3-diazo-4-oxo-3,4-dihydro-1-naphthalenyl)sul-
fonyl]oxyphenyl)-1-ethylpropyl]phenyl 3-diazo-4-oxo-
3,4-dihydro-1-naphthalenesulfonate (23);

4-[1-(4-[(3-diazo-4-oxo-3,4-dihydro-1-naphthalenyl)sul-
fonyl]oxyphenyl)-1,3-dimethylbutyl]phenyl 3-diazo-4-
oxo-3,4-dihydro-1-naphthalenesulfonate (24);

4-[1-(4-[(3-,diazoˆoxo-3,4-dihydro-1-naphthalenyl)sulfo-
nyl]oxyphenyl) cyclopentyl]phenyl 3-diazo-4-oxo-3,4-
dihydro-1-naphthalenesulfonate (25).

\* \* \* \* \*